(12) United States Patent
Lin (10) Patent No.: US 11,021,800 B2
(45) Date of Patent: Jun. 1, 2021

(54) ELECTROLYTIC DEVICE

(71) Applicant: Hsin-Yung Lin, Taoyuan (TW)

(72) Inventor: Hsin-Yung Lin, Taoyuan (TW)

( * ) Notice: Subject to any disclaimer, the term of this patent is extended or adjusted under 35 U.S.C. 154(b) by 0 days.

(21) Appl. No.: 15/750,148

(22) PCT Filed: Aug. 3, 2016

(86) PCT No.: PCT/CN2016/092997
§ 371 (c)(1),
(2) Date: Feb. 2, 2018

(87) PCT Pub. No.: WO2017/020824
PCT Pub. Date: Feb. 9, 2017

(65) Prior Publication Data
US 2018/0223440 A1  Aug. 9, 2018

(30) Foreign Application Priority Data

Aug. 5, 2015  (CN) .......................... 201520581251.3

(51) Int. Cl.
| | |
|---|---|
| *C25B 11/036* | (2021.01) |
| *C25B 1/04* | (2021.01) |
| *C25B 9/63* | (2021.01) |
| *C25B 11/00* | (2021.01) |
| *C25B 11/051* | (2021.01) |
| *C25B 11/081* | (2021.01) |
| *A61K 33/00* | (2006.01) |

(52) U.S. Cl.
CPC .............. *C25B 11/036* (2021.01); *C25B 1/04* (2013.01); *C25B 9/63* (2021.01); *C25B 11/00* (2013.01); *C25B 11/051* (2021.01); *C25B 11/081* (2021.01); *A61K 33/00* (2013.01); *Y02E 60/36* (2013.01)

(58) Field of Classification Search
CPC ...... C25B 1/02–1/12; C25B 1/06; C25B 1/04; C25B 1/042; C25B 1/044
See application file for complete search history.

(56) References Cited

U.S. PATENT DOCUMENTS

| | | | |
|---|---|---|---|
| 3,361,653 A | * | 1/1968 | Miller ....................... C25B 3/00 205/413 |
| 4,336,122 A | | 6/1982 | Spirig |

(Continued)

FOREIGN PATENT DOCUMENTS

| | | |
|---|---|---|
| CA | 2994358 | 2/2017 |
| CN | 2448850 | 9/2001 |

(Continued)

OTHER PUBLICATIONS

Search Report dated Apr. 2, 2019 for European Application No. 16832312.9.

(Continued)

*Primary Examiner* — Ciel P Contreras (57) ABSTRACT

The present invention provides an electrolytic device and includes an electrolytic tank and a plurality of electrodes. The electrolytic tank comprises a case for accommodating liquid water. The inner wall of the case has a plurality of engagement structures. The plurality of electrodes are set in the engagement structures respectively to be arranged at intervals in the case, wherein the case is connected to the plurality of electrodes by injection molding.

7 Claims, 7 Drawing Sheets

(56) References Cited

U.S. PATENT DOCUMENTS

| | | | |
|---|---|---|---|
| 5,292,405 A | 3/1994 | Wicks | |
| 5,690,797 A * | 11/1997 | Harada | C25B 1/12 204/228.5 |
| 8,449,737 B2 | 5/2013 | Richardson | |
| 2002/0166546 A1 * | 11/2002 | Andrews | B01D 53/9454 123/556 |
| 2004/0040838 A1 * | 3/2004 | Helmke | C25B 1/12 204/275.1 |
| 2005/0217991 A1 * | 10/2005 | Dahlquist, Jr. | C25B 1/04 204/267 |
| 2009/0205971 A1 * | 8/2009 | Pentz | C25B 1/04 205/341 |
| 2010/0065419 A1 * | 3/2010 | Richardson | C25B 1/04 204/228.2 |
| 2010/0276279 A1 * | 11/2010 | Arnett | C25B 1/06 204/274 |
| 2011/0272277 A1 | 11/2011 | Potchen et al. | |

FOREIGN PATENT DOCUMENTS

| | | |
|---|---|---|
| CN | 102618881 | 8/2012 |
| CN | 103255432 | 8/2013 |
| CN | 204999979 | 1/2016 |
| JP | H08173963 | 7/1996 |
| JP | 2001321769 | 11/2001 |
| JP | 2004143481 | 5/2004 |
| JP | 4302386 | 7/2009 |
| JP | 2010150590 | 7/2010 |
| JP | 2012091981 | 5/2012 |
| KR | 20090109218 A | 10/2009 |
| WO | WO2012125683 | 9/2012 |
| WO | WO2017020824 | 2/2017 |

OTHER PUBLICATIONS

Seach Report and Written Opinion dated Nov. 2, 2016 for PCT Application No. PCT/CN2016/092997.

Written Opinion dated Jul. 26, 2018 for Singapore Application No. 11201800843P.

* cited by examiner

ELECTROLYTIC DEVICE

CROSS-REFERENCE TO RELATED APPLICATIONS

This application is a U.S. National Phase of International Application No. PCT/CN2016/092997, filed Aug. 3, 2016 which claims the priority benefit of Chinese Application Serial No. 201520581251.3 filed Aug. 5, 2015 the disclosure of which is incorporated herein by reference.

BACKGROUND OF THE INVENTION

1. Field of the Invention

The present invention relates to an electrolytic device, and more particularly, to an electrolytic device for electrolyzing liquid water and generating hydrogen-oxygen gas.

2. Description of the Prior Art

People are always paying much attention on health developments. Many developments in medical technology are often targeted towards treating diseases and prolonging human life. Most of the treatments in the past are passive, which means that the disease is only treated when the disease occurs. The medical treatments include an operation, a medication treatment, a radiation therapy, or even medical treatment for cancer. But in recent years, most of the researches from medical experts are gradually moving towards preventive medical methods, such as research on healthy food, screening and preventing inherited diseases, which actively prevents diseases from occurring in the future. Because of this focus on prolonging human life, many anti-aging and anti-oxidation technologies including skin care products and anti-oxidation food/medicine are gradually being developed and have become increasingly popular to the general public.

Studies have found that there are instable oxygen species (O+), also known as free radicals, in the human body. The free radicals are usually generated due to diseases, diet, environment and one's lifestyle, but can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are also clinical experiments showing that patients who need to inhale a high concentration of oxygen for an extended period of time would experience lung damage and the lung damage could be ameliorated by inhaling hydrogen. In conclusion, hydrogen-containing gas can be regarded as a kind of health gas, and be generated by liquid water.

Figure 7:
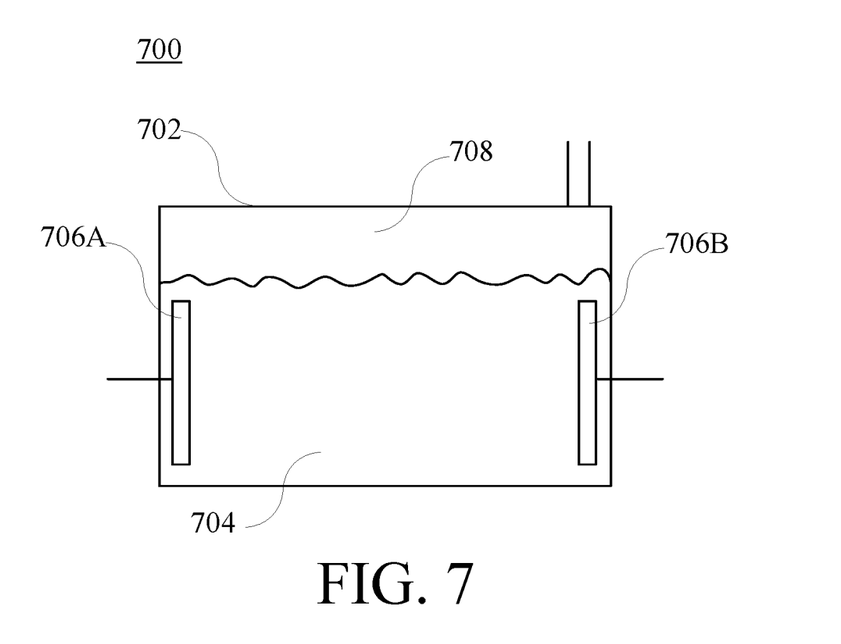
FIG. 7 shows a schematic diagram of the structure of the traditional electrolytic device.

Please refer to FIG. 7, FIG. 7 shows a schematic diagram of the structure of the traditional hydrogen-oxygen electrolytic device 700. The electrolytic device 700 comprises an electrolytic tank 702. The electrolytic tank 702 comprises electrodes 706A and 706B. The electrodes 706A and 706B are a negative electrode and a positive electrode respectively, coupled to a power source (not shown in FIG. 7) for supplying power to electrolyze water. The electrolytic water 704 in the electrolytic tank 702 is going to be electrolyzed when going through the electrified electrodes 706A and 706B. And then the negative pole will generate hydrogen and the positive pole will generate oxygen. The generated hydrogen and oxygen will be released on the top of the electrolytic tank 702 and then forms a hydrogen-oxygen mixed gas 708. The hydrogen-oxygen mixed gas 708 is outputted from the outputting tube of the electrolytic tank 702 for consequent use. However, the quantity of the hydrogen-oxygen gas generated from this kind of electrolytic device is normally limited by the shape and structure of the electrolytic tank.

SUMMARY OF THE INVENTION

An object of the present invention is to provide an electrolytic device includes an electrolytic tank and a plurality of electrodes. The electrolytic tank comprises a case. The case is used for accommodating liquid water. An inner wall of the case has a plurality of engagement structures. A plurality of electrodes are set in the engagement structures respectively to be arranged at intervals in the case. The case is connected to the plurality of electrodes by injection molding.

The electrolytic tank can selectively comprise an upper plate, configured on each top of the electrodes, and the upper plate comprises a plurality of protrusions, configured in a gap between the two corresponding electrodes, wherein the upper plate is made of insulation material.

The upper plate can selectively comprise a plurality of holes, corresponded to the gap between the two electrodes. The insulation material can selectively be rubber.

The electrolytic tank can selectively comprise a lower plate, configured on each bottom of the electrodes, and the lower plate is made of insulation material.

An interval between the bottom of the case and the electrodes is equal to or greater than 1 cm.

The interval between the bottom of the case and the electrodes can selectively be between 3 cm to 4 cm.

The electrolytic tank can selectively comprise a plurality of upper holes, and an electrode channel is formed between the two adjacent electrodes, wherein the electrode channel is corresponded to at least one of the upper holes respectively, and the electrode channel is connected to the outside through corresponding upper holes respectively.

The electrolytic tank can selectively comprise a plurality of lower holes, and an electrode channel is formed between the two adjacent electrodes, wherein the electrode channel is corresponded to at least one of the lower holes respectively, and the electrode channel is connected to the outside through the corresponding lower holes respectively.

The plurality of electrodes can selectively comprise a negative pole, a positive pole, and a plurality of bipolar electrodes. The plurality of bipolar electrodes are configured between the negative pole and the positive pole at intervals.

The voltage difference of a set of electrolytic electrodes constituted by the two adjacent bipolar electrodes is between 1.5V to 3V.

The negative pole and the positive pole have a rough surface respectively.

The negative pole and the positive pole can comprise a gold-plated bulge respectively, and the negative pole and the positive pole are connected to a power source through the bulge respectively.

The distance between the two adjacent electrodes can selectively be between 2 mm to 4 mm.

The distance between the two adjacent electrodes can selectively be 3 mm.

In conclusion, an object of the present invention is to provide an electrolytic device. The electrolytic device of the present invention can reduce power consumption and the volume of the case through setting the plurality of electrodes in the engagement structures respectively to be arranged at intervals in the case, and the distance between the two adjacent electrodes is between 2 mm to 4 mm. The interval between the bottom of the case and the electrodes is equal to or greater than 1 cm to avoid the electrodes point discharging within the electrolytic tank. The case can be combined closely with the plurality of electrodes to reduce the volume of the case through configuring the plurality of electrodes in the mold and then forming the case by injection molding.

BRIEF DESCRIPTION OF THE APPENDED DRAWINGS

Some of the embodiments will be described in detail, with reference to the following figures, wherein like designations denote like members, wherein.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1A:
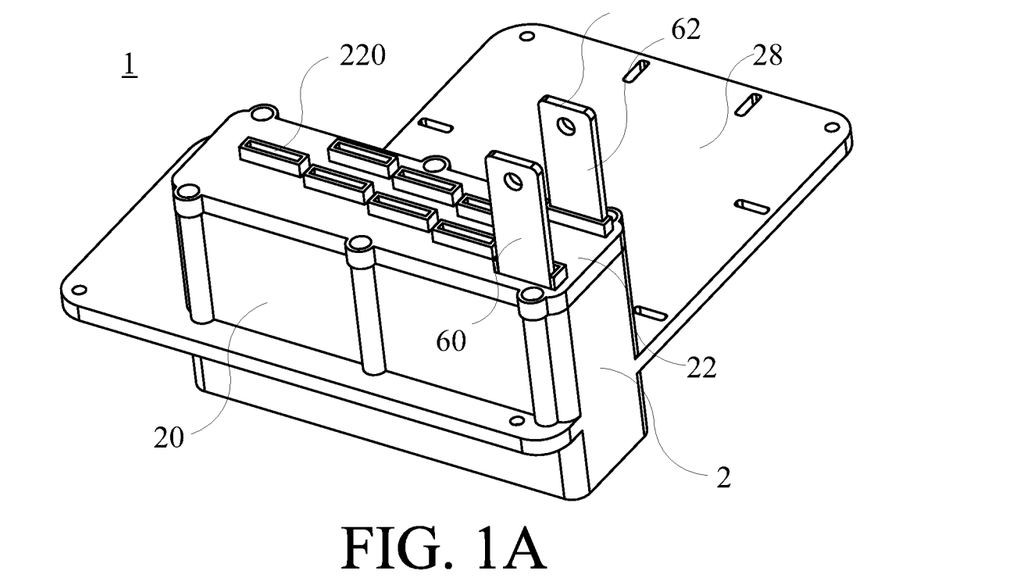
FIG. 1A and FIG. 1B show a schematic diagram of the electrolytic device in an embodiment with different visual angles of the present invention.
Figure 1B:
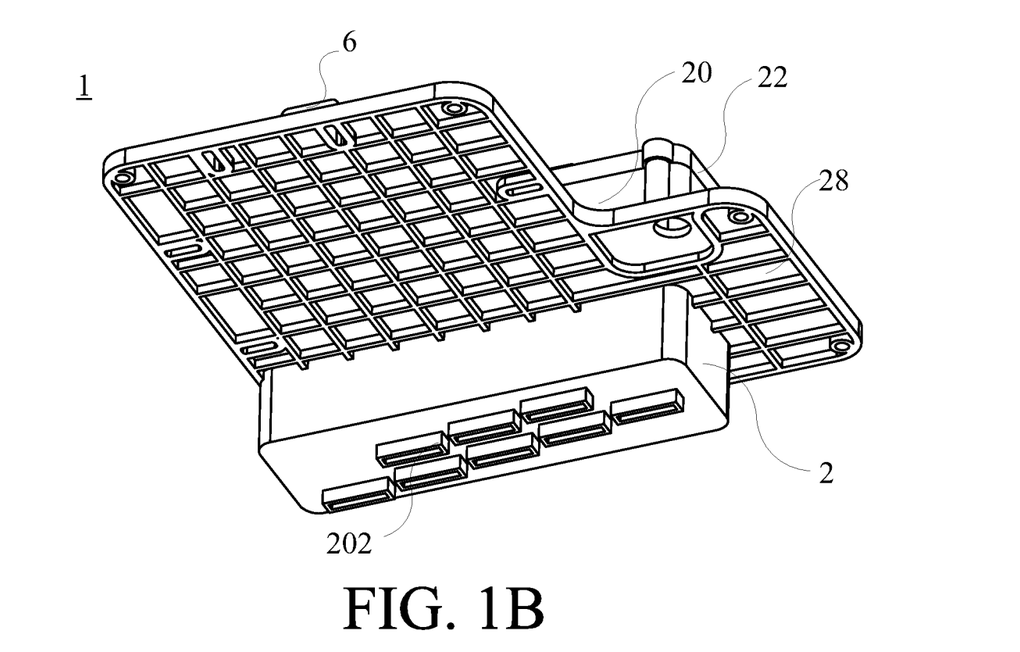

Please refer to FIG. 1A and FIG. 1B. FIG. 1A and FIG. 1B show a schematic diagram of the electrolytic device 1 in an embodiment with different visual angles of the present invention. FIG. 1A and FIG. 1B show the overall appearance of the electrolytic device. The electrolytic device 1 comprises an electrolytic tank 2 and a plurality of electrodes 6. The plurality of electrodes 6 comprise a negative pole 60 and a positive pole 62. In application, the negative pole 60 and the positive pole 62 are connected to an external power source (not shown in the figure) respectively, and the negative pole is connected to the cathode and the positive pole is connected to the anode. The plurality of electrodes 6 electrolyze the liquid water between the plurality of electrodes 6 and the electrolytic tank 2 to generate hydrogen-oxygen gas. The following statement will explain the design of each unit of the present invention respectively.

Figure 2A:
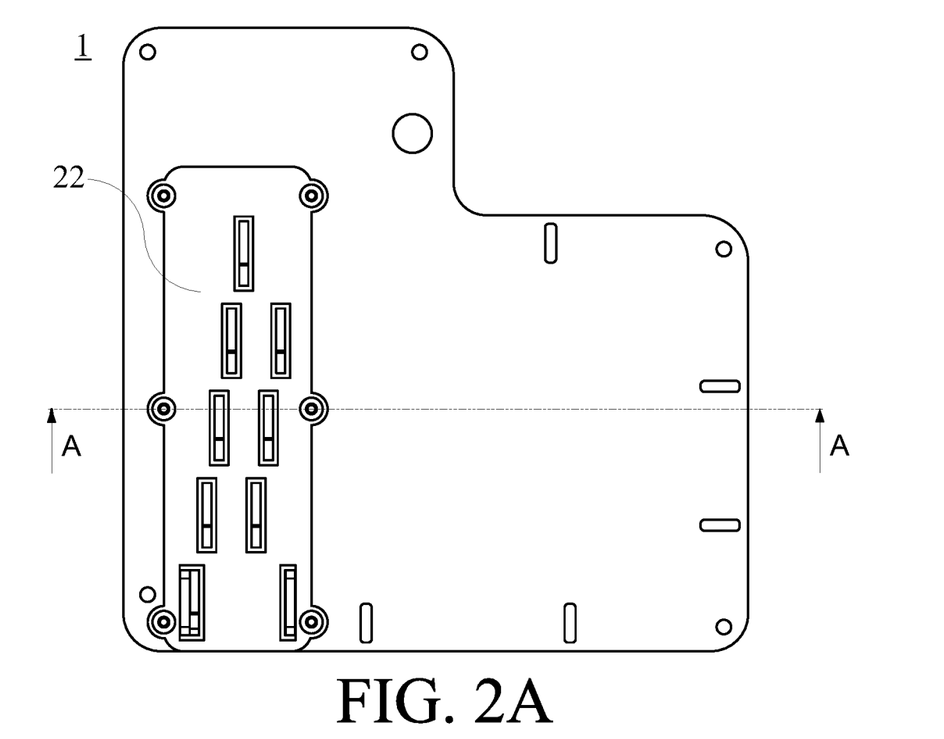
FIG. 2A and FIG. 2B show a top view diagram and a cross-section diagram crossing along to the A-A line in the top view diagram of the electrolytic device in the embodiment in FIG. 1A of the present invention.
Figure 2B:
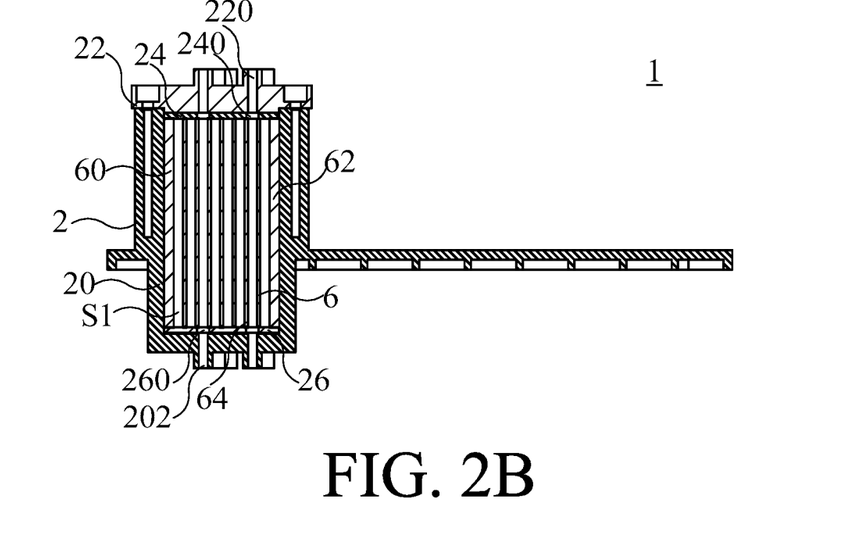

First, please refer to FIG. 2A and FIG. 2B. FIG. 2A and FIG. 2B show a top view diagram and a cross-section diagram crossing along to the A-A line in the top view diagram of the electrolytic device in the embodiment in FIG. 1A of the present invention. The electrolytic tank 2 comprises a case 20 used for accommodating liquid water. The plurality of electrodes 6 are arranged at intervals in the case 20.

Figure 3A:
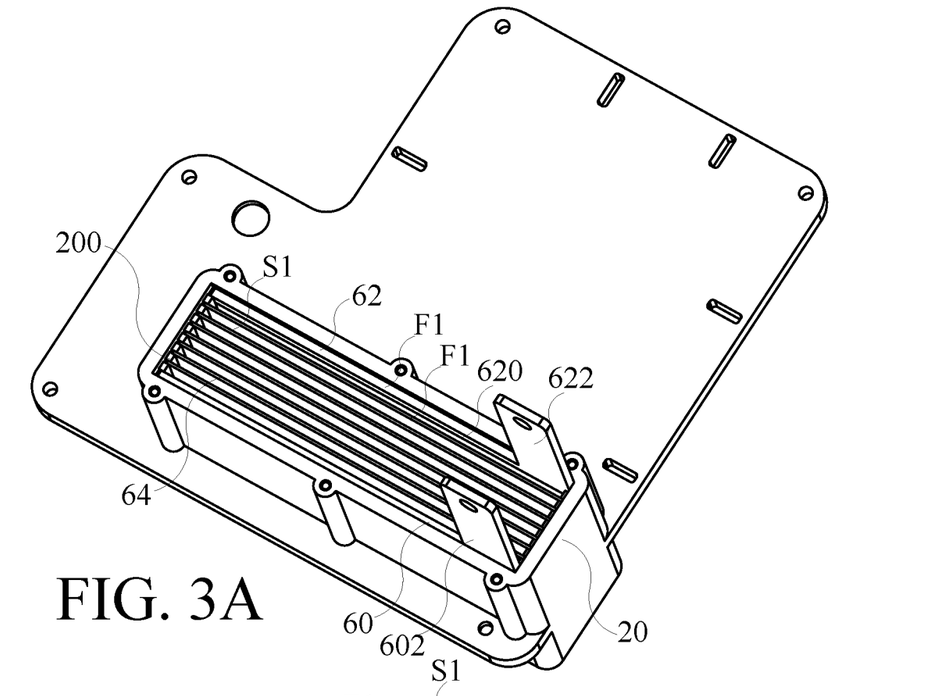
FIG. 3A and FIG. 3B show a schematic diagram of the case with engagement structures of the electrolytic device in an embodiment with different visual angles of the present invention.
Figure 3B:
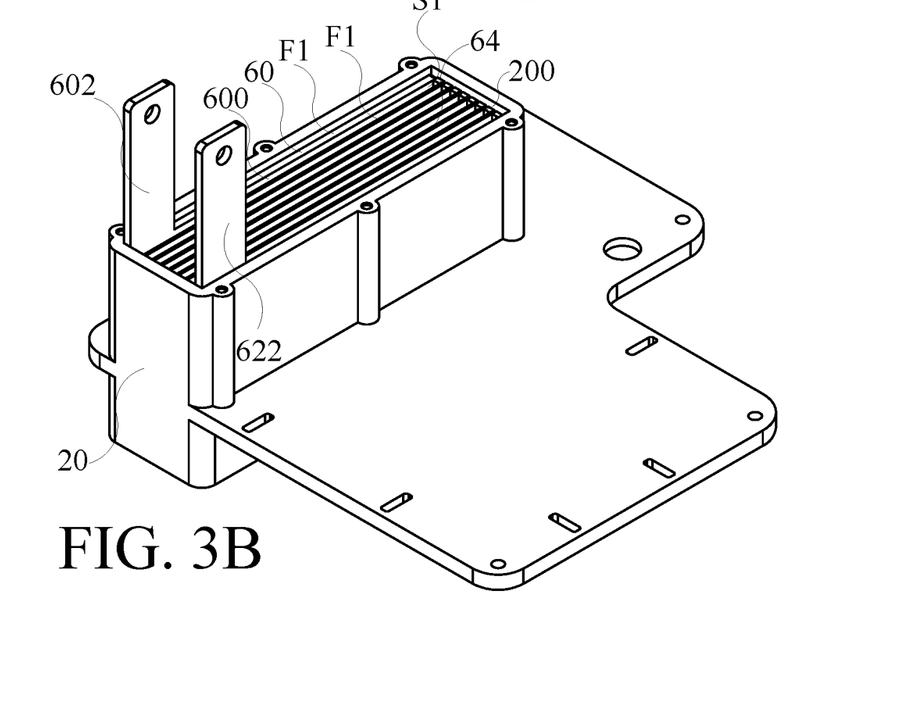

Please refer to FIG. 3A and FIG. 3B. FIG. 3A and FIG. 3B show a schematic diagram of the case with engagement structures of the electrolytic device in an embodiment with different visual angles of the present invention. The case 20 is connected to the plurality of electrodes 6 by injection molding. In an embodiment of the present invention, the case 20 can be formed by configuring the plurality of electrodes 6 in the mold and then proceeding injection molding. Namely, by injecting the case material which the designer needs, such as rubber, into the mold contacting with the electrodes closely to form the case 20 combined closely with one or a plurality of electrodes, the problem of time-consuming and labour-consuming due to inserting the electrodes piece by piece into the accommodating space of the case is solved. At the same time, the problem of the difficulty of inserting the electrodes piece by piece into the case because of the requirement of the smaller electrode interval is solved as well. Therefore, the assembly and production of the electrolytic device are more convenient, the low-cost mass production is easier, and the even electrode interval is provided so that the electrode arrangement is easier to be in the precise position. Besides, the reduction of power consumption can reduce the volume of the case when the electrode interval reduces.

Please refer to FIG. 3A and FIG. 3B. The inner wall of the case 20 comprises a plurality of engagement structures 200, wherein the plurality of electrodes 6 are set in the engagement structures 200 respectively to be arranged at intervals in the case 20 to form a plurality of electrode channels S1. The interval between the two adjacent electrodes is 3 mm so that not only power consumption but also volume of the case can be reduced; moverover, electrolytic efficiency can be raised. But in application, it is not limited to the above mentioned description; the interval between the two adjacent electrodes can also be between 2 mm to 4 mm. In an embodiment of the present invention, the plurality of engagement structures 200 can be one-piece formed with the case 20 by injection molding.

Figure 4A:
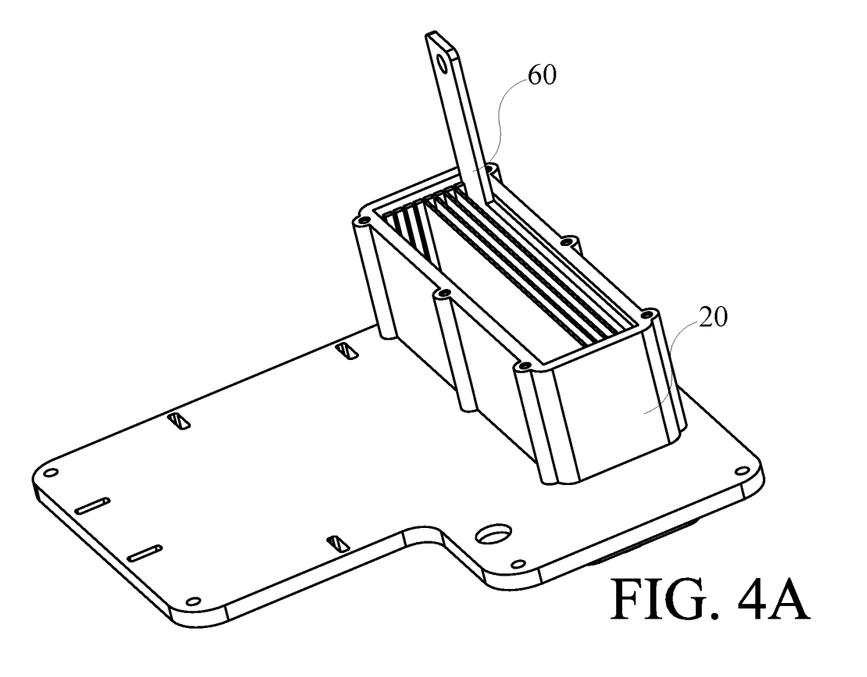
FIG. 4A and FIG. 4B show a schematic diagram of the case set with part of the electrodes of the electrolytic device in an embodiment with different visual angles of the present invention.
Figure 4B:
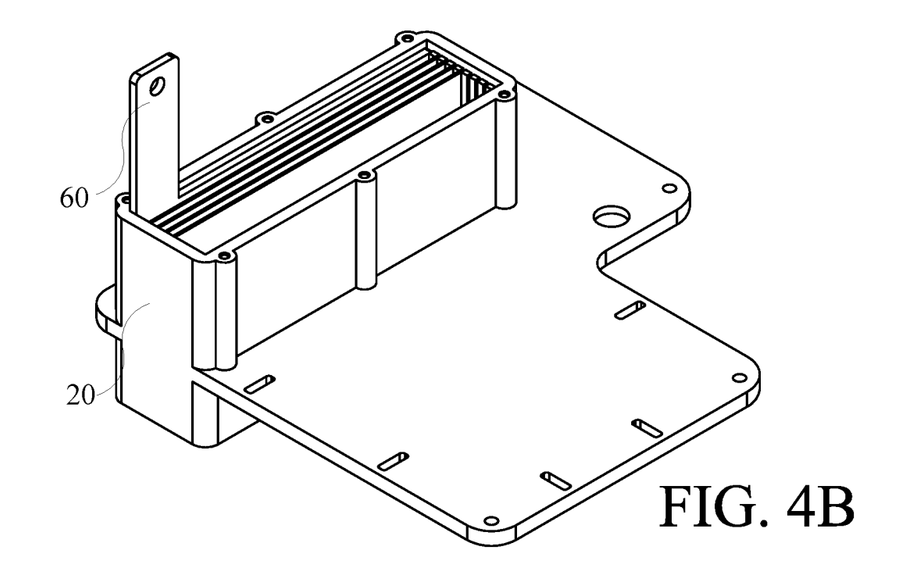

Please refer to FIG. 4A and FIG. 4B. FIG. 4A and FIG. 4B show a schematic diagram of the case set with part of the electrodes of the electrolytic device in an embodiment with different visual angles of the present invention. Compared FIG. 2A and FIG. 2B with FIG. 4A and FIG. 4B, it is easier to observe the overall appearance of the engagement structures without the electrodes. But the number or the appearance of the engagement structures is not limited to FIG. 4A and FIG. 4B. In application, the number of the engagement structures can be adjusted according to the number of the electrodes, or the designer can choose the number or the appearance of the engagement structures according to practical requirements.

In an embodiment of the present invention, the engagement structures 200 can be a bump or a groove. The bump is formed by extending from the inner wall of the case 20 to the outside. The groove is formed by indenting from the inner wall of the case 20. In an embodiment of the present invention, the plurality of electrodes 6 can be set between the two bumps at the both sides of the inner wall of the case respectively by being arranged at intervals in the case to form a plurality of electrode channels S1. The diameter of the bump is between 2 mm to 4 mm; namely, the interval between the two adjacent electrodes is between 2 mm to 4 mm. In a better embodiment of the present invention, the diameter of the bump is 3 mm; namely, the interval between the two adjacent electrodes is 3 mm. In another embodiment of the present invention, the plurality of electrodes 6 can be set between the two grooves at the both sides of the inner wall of the case respectively by being arranged at intervals in the case to form a plurality of electrode channels S1. The distance between the two grooves is between 2 mm to 4 mm; namely, the interval between the two adjacent electrodes is between 2 mm to 4 mm. In a better embodiment of the present invention, the distance between the two grooves is 3 mm; namely, the interval between the two adjacent electrodes is 3 mm.

Figure 5A:
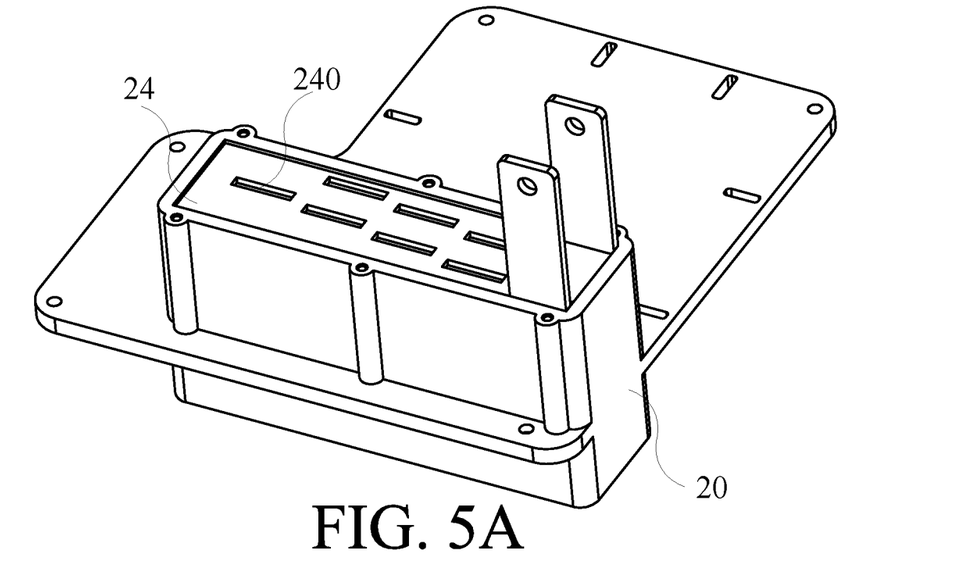
FIG. 5A and FIG. 5B show a schematic diagram of the electrolytic tank with an upper plate of the electrolytic device in an embodiment with different visual angles of the present invention.
Figure 5B:
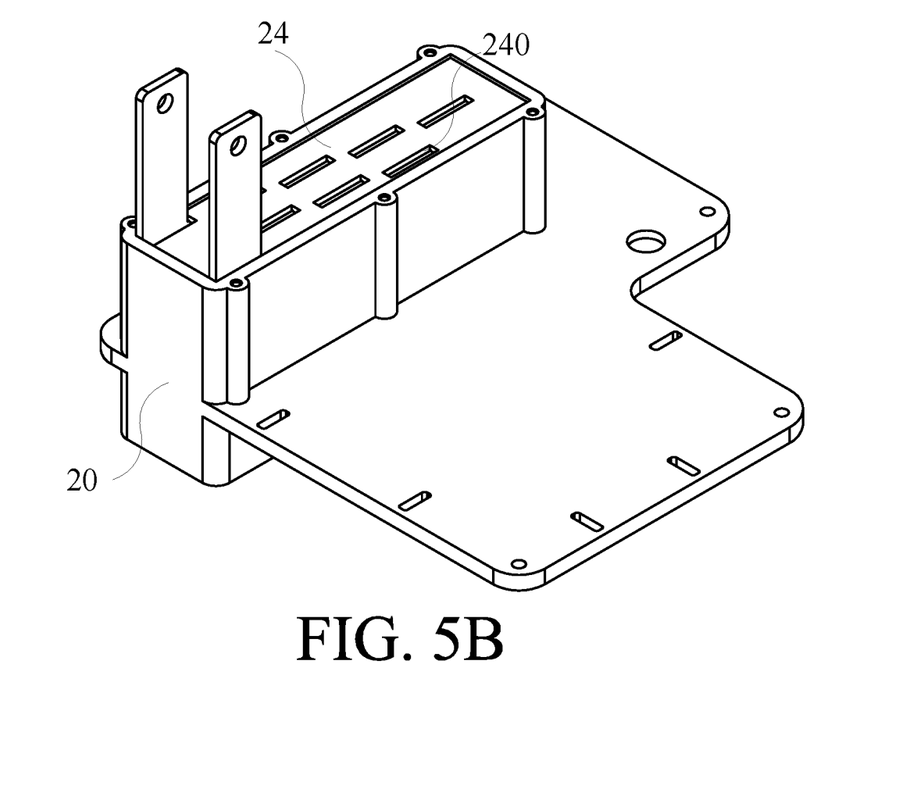

Please refer to FIG. 3A, FIG. 3B, FIG. 5A and FIG. 5B. FIG. 5A and FIG. 5B show a schematic diagram of the electrolytic tank with the upper plate 24 of the electrolytic device in an embodiment with different visual angles of the present invention. As FIG. 3A and FIG. 3B show, in an embodiment of the present invention, the top of the case 20 comprises an opening, and the electrode channels can be connected to the outside through the opening. Please refer to FIG. 5A and FIG. 5B in an embodiment of the present invention, the electrolytic tank further comprises an upper plate 24. The upper plate can be configured on the top of the electrolytic tank above the each upper surface F1 of the electrodes to close the opening. In an embodiment of the present invention, the upper plate comprises a plurality of protrusions, and the plurality of protrusions can be formed on the surface of the upper plate relatively to the electrode channels. When the upper plate is configured above the each upper surface F1 of the electrodes, the protrusions can be configured between the gap of the two electrodes to isolate the two adjacent electrodes. In an embodiment of the present invention, the gap between the two electrodes is the electrode channels S1. The upper plate can be, but not limited to, a rubber mat; in application, the upper plate can be anything that is made of insulation material. The upper plate 24 further comprises a plurality of upper holes 240 corresponded to the gap between the two electrodes. In an embodiment of the present invention, the gap between the two electrodes is the electrode channels S1. But the exterior and the number of the upper holes 240 is not limited to FIG. 5A and FIG. 5B. The electrode channels S1 are corresponded to at least one of the upper holes 240, and the electrode channels S1 are connected to the corresponding upper holes 240 independently. The upper holes 240 of the upper plate 24 are connected to the outside, so each electrode channel S1 can be connected to the outside independently. Therefore, the upper holes can output the hydrogen-oxygen gas generated by electrolyzing the liquid water from the case, but not limited to this. The upper holes 240 can even allow the liquid water from the outside to get inside the case and then flow into the electrode channels S1. Besides, the upper holes 240 can be penetrated by the negative pole and the positive pole, so that the negative pole and the positive pole can be connected to the power source (not shown in the figure).

In an embodiment of the present invention, the bottom of the case 20 comprises an opening (not shown in FIG. 3A and FIG. 3B, and the exterior is the same as the opening on the top in FIG. 3A and FIG. 3B), and the electrode channels can be connected to the outside through the opening. In an embodiment of the present invention, the electrolytic tank further comprises a lower plate (not shown in FIG. 5A and FIG. 5B, and the exterior and the setting way are the same as the upper plate in FIG. 5A and FIG. 5B). The lower plate can be configured on the bottom of the electrolytic tank below the each lower surface of the electrodes (relative to the lower surface of the electrodes) to close the opening. In an embodiment of the present invention, the lower plate comprises a plurality of protrusions, and the plurality of protrusions can be formed on the surface of the lower plate relatively to the electrode channels. When the lower plate is configured below the each lower surface of the electrodes, the protrusions can be configured between the gap of the two electrodes to isolate the two adjacent electrodes. In an embodiment of the present invention, the gap between the two electrodes is the electrode channels S1. The lower plate can be, but not limited to, a rubber mat; in application, the lower plate can be anything that is made of insulation material. The lower plate further comprises a plurality of lower holes corresponded to the gap between the two electrodes. In an embodiment of the present invention, the gap between the two electrodes is the electrode channels S1. The electrode channels S1 are corresponded to at least one of the lower holes, and the electrode channels S1 are connected to the corresponding lower holes independently. The lower holes of the lower plate are connected to the outside, so each electrode channel S1 can be connected to the outside independently. Therefore, the lower holes can allow the liquid water from the outside to get inside the case 20 and then flow into the electrode channels S1.

In an embodiment of the present invention, the electrolytic device can be configured in the water tank, even set firmly in the water tank dangly. The water tank comprises a hollow space for accommodating liquid water. The hollow space of the water tank can be connected to the electrode channels through the upper holes of the electrolytic tank so that the hydrogen-oxygen gas generated by electrolyzing the liquid water can be outputted from the case through the upper holes, and the liquid water can even enter the case and then get into the electrode channels S1 through the upper holes and the water tank. The hollow space of the water tank can be connected to the lower holes, so the liquid water can get inside the case and then flow into the electrode channels S1 through the lower holes and the water tank.

Please refer to FIG. 1B and FIG. 2B again. In another embodiment of the present invention, the case is a groove. As FIG. 1B shows, the electrolytic tank 2 further comprises a plurality of lower holes 202. The lower holes 202 can penetrate through the inside surface and the outside surface of the case 20. As FIG. 2B shows, an electrode channel S1 is formed between the two adjacent electrodes 6. The electrode channels S1 are corresponded to lower holes 202 respectively and connected to the corresponding lower holes on the bottom of the case 20 independently. But it is not limited to the above and the lower holes shown in FIG. 2B. In application, the electrode channels can also be corresponded to at least one of the lower holes respectively; namely, the designer can choose the exterior and the number of the lower holes corresponded to the electrode channels according to the actual demand. Each electrode channel can be connected to the outside through the corresponding lower holes 202 independently, so the lower holes 202 can allow the liquid water from the outside to get inside the case 20 and then flow into the electrode channels S1.

Please refer to FIG. 2B again. As FIG. 2B shows, the distance between the bottom of the case 20 and the electrodes 6 is between 3 cm to 4 cm to avoid the electrodes point discharging within the electrolytic tank. But it is not limited to the above, in application, the distance between the bottom of the case and the electrodes can be greater than 1 cm. In an embodiment of the present invention, a lower plate 26 is configured between the bottom of the case 20 and the electrodes 6. The lower plate 26 is set between the inner surface of the bottom of the case 20 and the lower surface of the electrodes 6 to avoid the distance between the electrodes 6 and the bottom of the case 20 being too close to cause the electrodes point discharging. In the embodiment of the present invention, the thickness of the lower plate is, but not limited to, between 3 cm to 4 cm, so that the distance between the bottom of the case and the electrodes is between 3 cm to 4 cm. In application, the thickness of the lower plate can be greater than 1 cm, so that the distance between the bottom of the case and the electrodes can be greater than 1 cm.

Furthermore, Please refer to FIG. 1B and FIG. 2B again. As FIG. 2B shows, the lower plate 26 further comprises a plurality of lower holes 260. The electrode channels S1 can be connected to the lower holes 202 of the bottom of the case 20 through the lower holes 260 of the lower plate 26 and can also be connected to the outside through the lower holes 260 and the lower holes 202. Therefore, the liquid water can enter inside the case 20 and then flow into the electrode channels S1 from the outside through the lower holes 202 and the lower holes 260.

In an embodiment of the present invention, the electrolytic tank further comprises a plurality of upper holes. As FIG. 2B shows, in an embodiment of the present invention, the electrolytic tank further comprises a upper plate 24 configured on each upper surface of the electrodes 6, wherein the upper plate 24 comprises a plurality of upper holes 240. As FIG. 2B shows, the electrode channels S1 are corresponded to at least one of the upper holes 240 respectively, and the electrode channels S1 are connected to the corresponding upper holes 240 independently. Furthermore, the upper holes 240 of the upper plate 24 are connected to the outside, so each electrode channel S1 can be connected to the outside independently. Therefore, the upper holes can output the hydrogen-oxygen gas generated by electrolyzing the liquid water from the case, but not limited to this. The upper holes can even allow the liquid water from the outside to get inside the case and then flow into the electrode channels S1. Beside, the upper holes can be penetrated by the negative pole and the positive pole, so that the negative pole and the positive pole can be connected to the power source (not shown in the figure).

Please refer to FIG. 1A and FIG. 1B again. In an embodiment of the present invention, as FIG. 1A shows, the electrolytic tank 2 further comprises a cover 22, wherein the cover 22 comprises a plurality of upper holes 220. But the number and the exterior of the upper holes 220 are not limited to FIG. 1A. As FIG. 2B shows, the cover 22 is configured on the case 20 and the upper plate 24, and the upper holes 220 of the cover 22 are connected to the upper holes 240 of the upper plate 24. The electrode channels S1 can be connected to the upper holes 220 of the cover 22 through the upper holes 240 of the upper plate 24, and the electrode channels S1 are connected to the outside through the upper holes 220, so that each electrode channel S1 can be connected to the outside independently. Therefore, the upper holes 240 of the upper plate 24 and the upper holes 220 of the cover 22 can output the hydrogen-oxygen gas generated by electrolyzing the liquid water from the case, but not limited to this. The upper holes 240 of the upper plate 24 and the upper holes 220 of the cover 22 can even allow the liquid water from the outside to get inside the case and then flow into the electrode channels S1. Beside, the upper holes 240 of the upper plate 24 and the upper holes 220 of the cover 22 can be penetrated by the negative pole and the positive pole, so that the negative pole and the positive pole can be connected to the power source.

In an embodiment of the present invention, the electrolytic device can be configured in the water tank, even set firmly in the water tank dangly. The water tank comprises a hollow space for accommodating liquid water. The hollow space of the water tank can be connected to the electrode channels through the upper holes of the electrolytic tank so that the hydrogen-oxygen gas generated by electrolyzing the liquid water can be outputted from the case through the upper holes, and the liquid water can even enter the case and then flow into the electrode channels S1 through the upper holes and the water tank. The hollow space of the water tank can be connected to the lower holes, and the liquid water can enter the case and then flow into the electrode channels S1 through the lower holes and the water tank.

In an embodiment of the present invention, the electrolytic tank 2 can comprise a separator 28 (shown in FIG. 1A). The separator 28 is formed from the side surface of the case 2 corresponded to the water tank extending to the outside. But the exterior of the separator 28 is not limited to the figures, in application, the exterior form can be chosen depending on the internal structure of the water tank. In an embodiment of the present invention, the separator 28 is, but not limited to, a one-piece formed with the case 20. In application, the user can also decide whether to configure the separator on the outside of the case according to the demand. In an embodiment of the present invention, the case and the separator are formed as a one-piece by a mold with the separator and the case construction processing injection molding. In an embodiment of the present invention, when the electrolytic tank is configured in the water tank, the electrolytic tank 2 can split the hollow space of the water tank into upper part and lower part through the separator 28. The upper part of the hollow space of the water tank can be connected to the upper holes of the electrolytic tank, and the hydrogen-oxygen gas generated by electrolyzing the liquid water can be outputted from the case through the upper holes, and the liquid water can even enter the case and then flow into the electrode channels S1 through the upper holes and the upper part of the hollow space of the water tank. The lower part of the hollow space of the water tank can be connected to the lower holes of the electrolytic tank, and the liquid water can enter the case and then flow into the electrode channels S1 through the lower holes and the lower part of the hollow space of the water tank.

Please refer to FIG. 2B and FIG. 6 again. In the embodiment of the present invention, the plurality of electrodes 6 are the negative pole 60, the positive pole 62, and the plurality of bipolar electrodes 64. The plurality of bipolar electrodes 64 are configured between the negative pole 60 and the positive pole 62 arranged at intervals. The negative pole 60 has a rough surface (shown in FIG. 6) and the positive pole 62 also has a rough surface (not shown in the figure). In an embodiment of the present invention, the electrolytic area of the negative pole 60 and the positive pole 62 are increased by the brushing method to roughen the surface of the negative pole and the positive pole.

Figure 6:
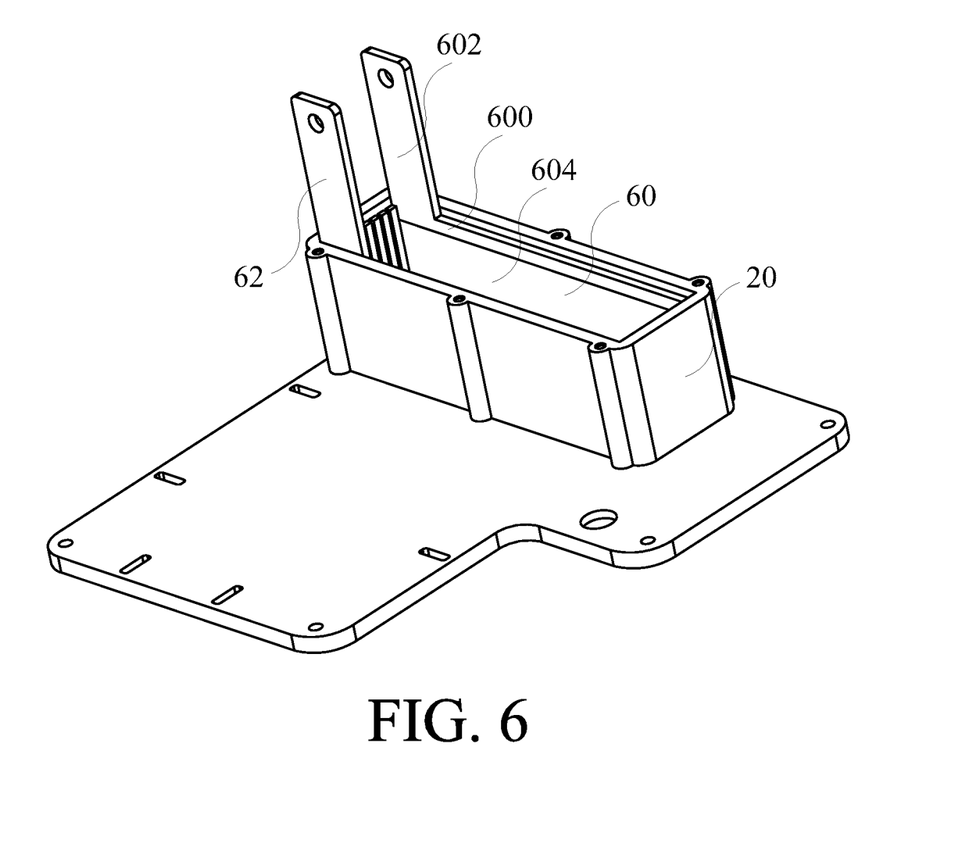
FIG. 6 shows a schematic diagram of the case of the electrolytic device configured with positive pole and negative pole in an embodiment of the present invention.

Please refer to FIG. 3A, FIG. 3B and FIG. 6. FIG. 6 shows a schematic diagram of the case of the electrolytic device configured with positive pole and negative pole in an embodiment of the present invention. In an embodiment of the present invention, the negative pole 60 comprises a metal layer 600 (shown in FIG. 3B and FIG. 6) and the positive pole 62 comprises a metal layer 620 (shown in FIG. 3A). The negative pole 60 and the positive pole 62 are connected to the power source (not shown in the figure) through the metal layer respectively. But the area size of the metal layer is not limited to FIG. 6 and can be adjust according to practical application. In an embodiment of the present invention, the negative pole and the positive pole can comprise a gold-plated bulge 602, 622 (shown in FIG. 3A and FIG. 3B) respectively, and the negative pole 60 and the positive pole 62 are connected to the power source through the bulge 602, 622 respectively.

When the electrolytic device is connected to the outside power source, the negative pole 60 can be connected to the cathode and the positive pole 62 can be connected to the anode, wherein the voltage difference of a set of electrolytic electrodes constituted by the two adjacent bipolar electrodes 64 is between 1.5V to 3V. The voltage difference of a set of electrolytic electrodes constituted by the negative pole 60 and the bipolar electrodes 64 is between 1.5V to 3V. The voltage difference of a set of electrolytic electrodes constituted by the bipolar electrodes 64 and the bipolar electrodes 64 is between 1.5V to 3V. The voltage difference of a set of electrolytic electrodes constituted by the bipolar electrodes 64 and the positive pole 62 is between 1.5V to 3V.

When the electrolytic device is connected to the outside power source, the output voltage difference of the power source is between 17V to 27V, and the output electric current of the power source is between 30 A to 40 A; namely, the electrolytic device generates air output between 1.5 L to 4.0 L per minute. The voltage difference of a set of electrolytic electrodes (between the cathode and the anode) in use is between 1.5V to 3V; for example, the voltage difference of eight sets of electrolytic electrodes in use is between 12V to 24V. But it is not limited to the above mentioned description. In application, when the electrolytic device is connected to the outside power source, the output voltage difference of the power source is between 5V to 27V, and the output electric current of the power source is between 2 A to 150 A; namely, the power of the power source is between 10 W (5V*2 A) and 3600 W (24V*150 A), and the electrolytic device generates air output between 0.01 L and 12 L per minute.

In conclusion, an object of the present invention is to provide an electrolytic device. The electrolytic device of the present invention can reduce power consumption and reduce the volume of the case and increase overall efficiency through setting the plurality of electrodes in the engagement structures respectively to be arranged at intervals in the case, and the distance between the two adjacent electrodes is between 2 mm to 4 mm. The interval between the bottom of the case and the electrodes is equal to or greater than 1 cm to avoid the electrodes point discharging within the electrolytic tank.

The case combined closely with the plurality of electrodes through configuring the plurality of electrodes in the mold and then forming the case by injection molding can solve the problem of time-consuming and labour-consuming due to inserting the electrodes piece by piece into the accommodating space of the case. Therefore, the assembly and production of the electrolytic device are more convenient, the low-cost mass production is easier, and the even electrode interval is provided so that the electrode arrangement is easier to be in the precise position.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. An electrolytic device comprising:
   a water tank comprising a hollow space for accommodating water;
   an electrolytic tank with a case configured in the hollow space of the water tank, the case of the electrolytic tank is configured for accommodating the water and an inner wall of the case having a plurality of engagement structures, the electrolytic tank comprising a separator extending outward from a side surface of the case to split the hollow space of the water tank into an upper part and a lower part; and
   a plurality of electrodes coupled to the plurality of engagement structures and arranged separately;
   wherein the plurality of electrodes are fixed to the case, and the electrolytic tank further comprises a cover configured above the case.

2. The electrolytic device of claim 1, wherein a bottom of the electrolytic tank comprises a plurality of lower holes fluidly coupled to the hollow space of the water tank.

3. The electrolytic device of claim 2, wherein an electrode channel is formed between two adjacent electrodes of the plurality of electrodes such that a set of electrode channels are formed within the plurality of electrodes, and the set of electrode channels are fluidly coupled to the plurality of lower holes.

4. The electrolytic device of claim 1, wherein the electrolytic tank further comprises an upper plate disposed on the plurality of electrodes, the upper plate is made of insulation material and comprises a plurality of protrusions disposed in a set of gaps formed within the plurality of electrodes.

5. The electrolytic device of claim 4, wherein the upper plate further comprises a plurality of holes penetrating through the upper plate, and the plurality of holes are corresponding to the set of gaps within the plurality of electrodes.

6. The electrolytic device of claim 5, wherein the cover is configured above the upper plate, and the cover comprises a plurality of upper holes fluidly coupled to the plurality of holes of the upper plate.

7. The electrolytic device of claim 6, wherein the upper part of the hollow space of the water tank is fluidly coupled to the upper holes of the cover.

* * * * *